(12) United States Patent
Goco

(10) Patent No.: US 10,973,504 B2
(45) Date of Patent: Apr. 13, 2021

(54) RETRACTOR SUCTION CATHETER

(71) Applicant: Paulino Edwardo Goco, Murfreesboro, TN (US)

(72) Inventor: Paulino Edwardo Goco, Murfreesboro, TN (US)

(*) Notice: Subject to any disclaimer, the term of this patent is extended or adjusted under 35 U.S.C. 154(b) by 618 days.

(21) Appl. No.: 15/468,513

(22) Filed: Mar. 24, 2017

(65) Prior Publication Data
US 2017/0196547 A1    Jul. 13, 2017

Related U.S. Application Data

(63) Continuation-in-part of application No. 14/451,541, filed on Aug. 5, 2014, now Pat. No. 9,649,416.

(51) Int. Cl.
| | | |
|---|---|---|
| *A61B 17/02* | (2006.01) | |
| *A61B 17/24* | (2006.01) | |
| *A61M 25/02* | (2006.01) | |
| *A61M 1/00* | (2006.01) | |
| *A61M 25/00* | (2006.01) | |
| *B08B 15/00* | (2006.01) | |
| *A61M 25/04* | (2006.01) | |

(52) U.S. Cl.
CPC .............. *A61B 17/02* (2013.01); *A61B 17/24* (2013.01); *A61M 1/008* (2013.01); *A61M 25/02* (2013.01); *A61B 2217/005* (2013.01); *A61M 25/0041* (2013.01); *A61M 25/04* (2013.01); *A61M 2025/022* (2013.01); *A61M 2025/024* (2013.01); *A61M 2025/0226* (2013.01); *A61M 2210/065* (2013.01); *A61M 2210/0618* (2013.01); *A61M 2210/0625* (2013.01); *B08B 15/007* (2013.01); *Y10S 128/26* (2013.01); *Y10S 604/902* (2013.01)

(58) Field of Classification Search
CPC .................................................... B08B 15/007
See application file for complete search history.

(56) References Cited

U.S. PATENT DOCUMENTS

| 1,374,430 | A | * | 4/1921 | Chevalier | .............. | A47K 3/287 |
| | | | | | | 4/618 |
| 4,133,315 | A | * | 1/1979 | Berman | .................. | A61F 5/004 |
| | | | | | | 604/909 |
| 4,417,874 | A | * | 11/1983 | Andersson | .............. | A61C 17/08 |
| | | | | | | 433/96 |

(Continued)

OTHER PUBLICATIONS

Naraghi, Mohsen, and Arash Kashfi. "Endoscopic resection of nasopharyngeal angiofibromas by combined transnasal and transoral routes." American journal of otolaryngology 24.3 (2003): 149-154 (Year: 2003).*

(Continued)

*Primary Examiner* — Guy K Townsend
(74) *Attorney, Agent, or Firm* — Dunlap Bennett & Ludwig, PLLC

(57) ABSTRACT

A retractor suction catheter used during surgery is provided. The suction catheter may include a flexible tube having an open end and a closed end. The open end may include a fitting. The tube may further include a plurality of slits in between the open end and the closed end. The tube may fit through a subject's oral cavity and out of the mouth. The tube may retract the soft palate so that the surgeon may perform the proper surgery. Further, a vacuum may be attached to the fitting, and therefore liquids, fumes and debris may be removed through the apertures.

10 Claims, 2 Drawing Sheets

(56) References Cited

U.S. PATENT DOCUMENTS

| | | | | | |
|---|---|---|---|---|---|
| 4,634,425 | A | * | 1/1987 | Meer | A61J 15/0003 128/207.18 |
| 4,778,448 | A | * | 10/1988 | Meer | A61J 15/003 128/207.18 |
| 5,279,599 | A | * | 1/1994 | Wilk | A61M 1/008 604/313 |
| 5,322,521 | A | * | 6/1994 | Wilk | A61M 1/008 433/91 |
| 5,492,538 | A | * | 2/1996 | Johlin, Jr. | A61M 25/0068 128/899 |
| 5,599,304 | A | * | 2/1997 | Shaari | A61M 1/008 604/173 |
| 5,941,873 | A | * | 8/1999 | Korenfeld | A61B 17/0231 604/313 |
| 6,702,788 | B2 | * | 3/2004 | Kawakita | A61M 25/007 604/264 |
| 8,435,261 | B2 | * | 5/2013 | Arcand | A61M 29/02 606/199 |
| 8,951,225 | B2 | * | 2/2015 | Evard | A61M 29/02 604/96.01 |
| 10,188,413 | B1 | * | 1/2019 | Morriss | A61M 25/0147 |
| 2003/0177695 | A1 | * | 9/2003 | Manning | A01G 25/02 47/48.5 |
| 2006/0032509 | A1 | * | 2/2006 | Milles | A61M 16/009 128/205.12 |
| 2007/0167682 | A1 | * | 7/2007 | Goldfarb | A61B 1/0014 600/114 |
| 2007/0208252 | A1 | * | 9/2007 | Makower | A61B 6/037 600/424 |
| 2009/0120446 | A1 | * | 5/2009 | Vaska | A61F 5/566 128/848 |
| 2010/0024830 | A1 | * | 2/2010 | Rousseau | A61F 5/566 128/848 |
| 2011/0220124 | A1 | * | 9/2011 | Vaska | A61F 5/566 128/848 |
| 2012/0136207 | A1 | * | 5/2012 | Goldfarb | G02B 6/4292 600/106 |
| 2013/0073015 | A1 | * | 3/2013 | Rozenberg | A61K 9/007 607/106 |
| 2013/0095450 | A1 | * | 4/2013 | Ames | A61C 17/08 433/93 |
| 2013/0111811 | A1 | * | 5/2013 | Miyauchi | A01G 9/246 47/57.7 |
| 2013/0312768 | A1 | * | 11/2013 | Flaherty | A61F 5/566 128/848 |
| 2013/0338521 | A1 | * | 12/2013 | Thompson | A61M 16/0484 600/532 |
| 2014/0276653 | A1 | * | 9/2014 | Brennan | A61M 27/00 604/540 |
| 2016/0038170 | A1 | * | 2/2016 | Goco | A61M 25/02 600/37 |
| 2017/0196547 | A1 | * | 7/2017 | Goco | A61M 1/008 |

OTHER PUBLICATIONS

Hoffman, Jason, J. Mark Matthews, and Adam R. Reese. "Oral endotracheal tube exchange to the nasal route in a patient with facial trauma." Journal of clinical anesthesia 23.4 (2011): 342. (Year: 2011).*

Naraghi, Mohsen, and Arash Kashfi. "Endoscopic resection of nasopharyngeal angiofibromas by combined transnasal and transoral routes." American journal of otolaryngology 24.3 (2003): pp. 149-154. (Year: 2003).*

Hoffman, Jason, J. Mark Matthews, and Adam R. Reese. "Oral endotracheal tube exchange to the nasal route in a patient with facial trauma." Journal of clinical anesthesia 23.4 (2011): p. 342. (Year: 2011) (Year: 2011).*

* cited by examiner

RETRACTOR SUCTION CATHETER

This application is a continuation in part of U.S. non-provisional application Ser. No. 14/451,541 filed Aug. 5, 2014, the contents of which are herein incorporated by reference.

BACKGROUND OF THE INVENTION

The present invention relates to a suction catheter and, more particularly, to a suction catheter that retracts the soft palate.

In medicine, a catheter is a thin tube extruded from medical grade materials serving a broad range of functions. Catheters are medical devices that can be inserted in the body to treat diseases or perform a surgical procedure. By modifying the material or adjusting the way catheters are manufactured, it is possible to tailor catheters for cardiovascular, urological, gastrointestinal, neurovascular, otolaryngic and ophthalmic applications Catheters can be inserted into a body cavity, duct, or vessel. Functionally, they allow drainage, administration of fluids or gases, access by surgical instruments, and also perform a wide variety of other tasks depending on the type of catheter. The process of inserting a catheter is catheterization. In most uses, catheter is a thin, flexible tube though catheters are available in varying levels of stiffness depending on the application.

When performing procedures on the back of the nose, nasopharynx and/or oral cavity through the mouth, it is necessary to hold back the soft palate to prevent the soft palate from blocking the working area. Further, it is advantageous to remove fluid, smoke or vapor produced during the procedure to visualize the surgical site. The current practice during surgeries such as Tonsillectomies and adenoidectomies is to use a small red rubber catheter through the nose and out of the mouth. The catheter is then tied to itself or held with a clamp. Then a second person usually must suction the fluids, vapors and/or smoke with a separate suction device interfering with visualization of the operating field. Using two devices in a small operating area is awkward and blocks visualization in the working area.

As can be seen, there is a need for an improved catheter used to perform the surgeries listed above.

SUMMARY OF THE INVENTION

In one aspect of the present invention, a suction catheter comprises: a flexible tube having a first end, a second end, and a cluster of openings or slits formed through the flexible tube in between the first end and the second end, wherein the first end comprises a closed end and the second end comprises a fitting formed to releasably secure to a vacuum hose, and the cluster of slits are biased in a closed position when the flexible tube is in a relaxed state, wherein when a tension is applied to the tube the cluster of slits deform from the closed position to an open position, forming a cluster of openings.

In another aspect of the present invention, a method of treatment comprising the steps of: providing a flexible tube comprising a first closed end, a second open end and a cluster of slits formed through the tube in between the first closed end and the second open end; inserting the first closed end through a nasal cavity, through an oral cavity and out of a mouth of a user; positioning the plurality of slits in between the oral cavity and the nasal cavity adjacent to a soft palate of the user; and pulling the tube against the soft palate, thereby retracting the soft palate and deforming the plurality of slits from a closed position to an open position.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a suction catheter used during surgery or other procedures. The suction catheter may include a tube having an open end and a closed end. The open end may include a fitting. The tube may further include a plurality of circumferential slits in between the open end and the closed end. The tube may fit through a subject's oral cavity and out of the mouth. The tube may be pulled to open the slits and retract the soft palate so that the healthcare provider may perform the proper procedure. Further, a vacuum may be attached to the fitting, and therefore fumes and debris may be removed through the opened slits. Further, a light source may be attached or built into the fitting, and therefore allow illumination of the surrounding areas. Further, a camera may be attached or built into the fitting and allow video or photos of the surrounding area. Further, a distal opening can be placed or made to allow suctioning as in a typical suction catheter.

The present invention includes a flexible non-conductive suction catheter that retracts the soft palate and suctions fluids/fumes/smoke. The catheter may hold the soft palate away from the surgical field and also act as a conduit to remove fluids, vapors and smoke that is produced during the surgery and also allow irritation of the surgical site. By utilizing one device to hold back soft tissue and provide suction, the present invention provides more room to visualize the procedure and further allows a single person to perform the procedure. The present invention may retract the soft palate and remove fluids/vapors/smoke thereby eliminating a separate second suction device used during surgery.

The present invention includes a flexible medical grade soft catheter with an end designed to attach to suction tubing with an opposite blunt end. Under general anesthesia, the blunt end may be inserted into the nose and comes out of the mouth. The catheter may then be secured to an attachment on the catheter exiting the nose or to a mouth guard to hold the soft palate out of the surgical field. The catheter may include a plurality of slits or openings placed circumferentially around the catheter. When tension is applied to the catheter, the slits open to allow suctioning of vapor and smoke away from the surgical field. After the surgery is completed the catheter may be removed.

Figure 1:
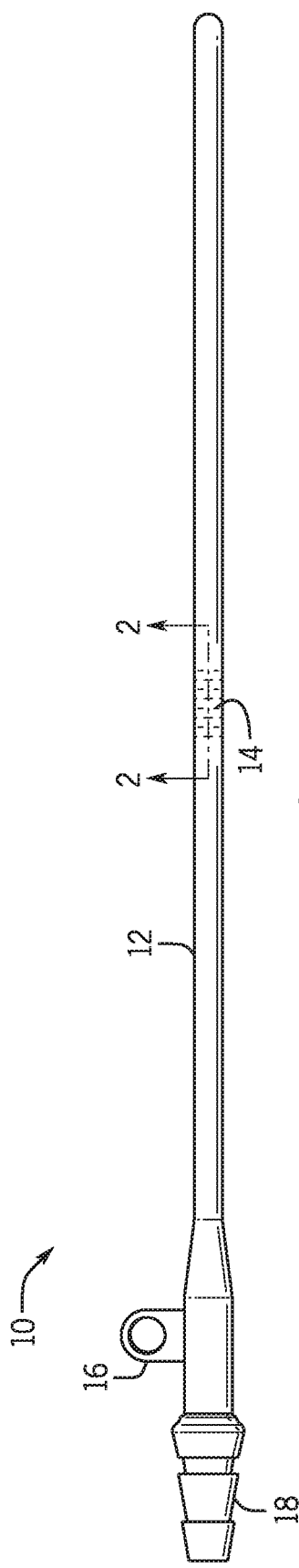
FIG. 1 is a side elevation view of an embodiment of the present invention demonstrating the present invention in an extended position.
Figure 2:
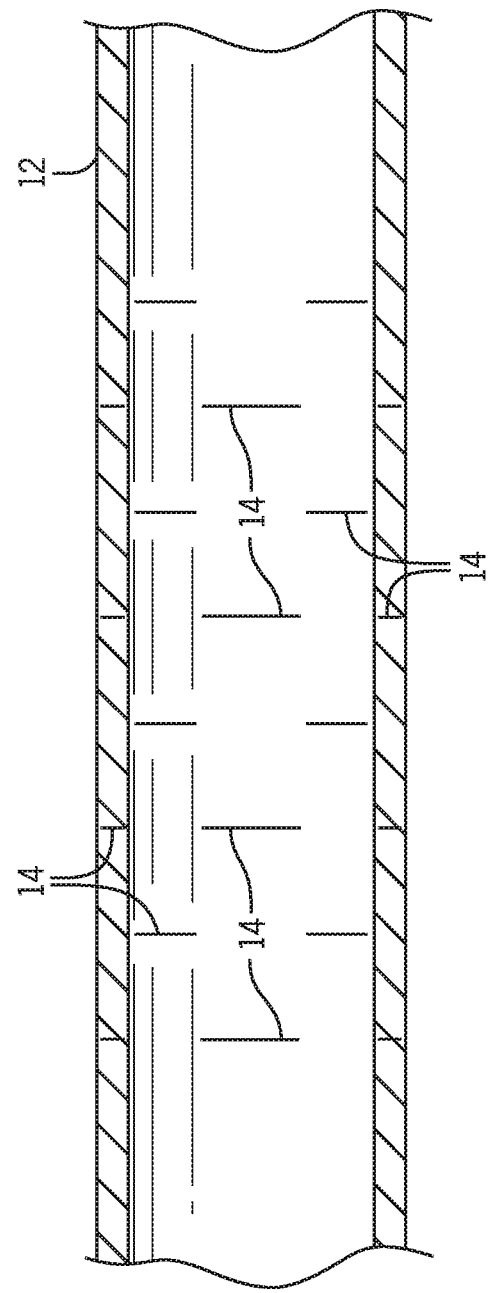
FIG. 2 is a cross-sectional detail view of the apertures taken along line 2-2 of FIG. 1.
Figures 3, 4:
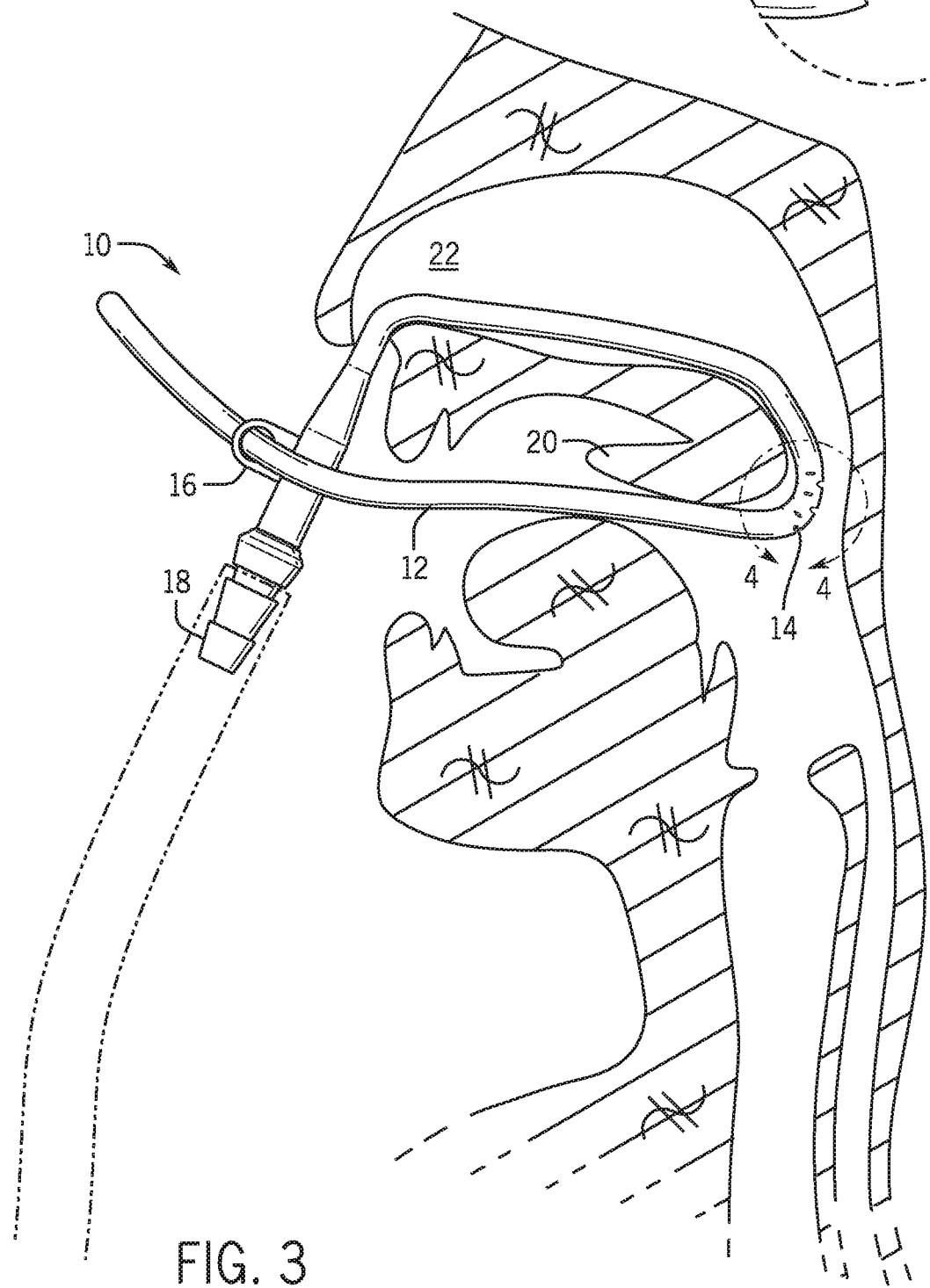
FIG. 3 is a side elevation view of the embodiment of FIG. 1 demonstrating the present invention in use.
FIG. 4 is a detail view from 4-4 of FIG. 3.

Referring to FIGS. 1 through 4, the present invention includes a suction catheter 10. The suction catheter 10 may include a flexible tube 12 with a first end and a second end. The tube 12 may further include at least one slit 14 through the tube 10 in between the first end and the second end. In certain embodiments, the first end of the tube 12 may be a closed end i.e. a blunt end, and the second end of the tube may be open and including a fitting 18 formed to releasably secure to a vacuum hose 24.

In certain embodiments, the suction catheter 10 of the present invention may include a reversible attachment mechanism 16. The attachment mechanism 16 may be attached to the tube 12 near the second end, and thereby near the fitting 18. The attachment mechanism 16 may extend from the tube 12 and may releasably attach to the tube 12. For example, the attachment mechanism 16 may releasably attach to the tube 12 to the first end in a looped position.

In certain embodiments, the attachment mechanism 16 may include any device that may attach a first portion of the tube 12 to a second portion of tube 12. As illustrated in the Figures, the attachment mechanism 16 may include a tab extending from the tube 12. An opening may be disposed through the tab. The tube 12 may be inserted into the opening and pulled through, and thereby attaching the tube 12 to itself in a looped position. However, the attachment mechanism 16 is not limited to a tab and may include clips, snaps, bands, and the like, so that opposite ends of the tube may releasably attach to one another. The attachment of the of tube 12 to itself may pull the soft palate 20 out of the way, as well as consolidate the tube 12 for convenient surgical performance.

In certain embodiments, the at least one slit 14 is located near a center point in between the first end and the second end. When in use, the slit 14 may be placed in between the oral cavity and the nasal cavity 22, such as near the soft palate 20. The at least one slit 14 may include a cluster of slits 14 oriented circumferentially around the tube 12. The cluster of slits 14 are oriented within a close proximity of one another and are centrally located in between the first end and the second end. When the catheter 10 is placed through the nasal cavity 22 and out the oral cavity, the blunt end is pulled through the tab to retract the soft palate 20. The tension from tightening the catheter 10 against the soft palate 20 deforms the slits 14 from a biased closed position to an open position. When the slits 14 are in the open positioned, smoke, fumes or other debris may vent from within the oral or nasal cavity 22.

The present invention may further include a method of treatment using the suction catheter described above. The method of treatment may include providing a tube having a first closed end and a second open end, with at least one slit disposed through the tube in between the first end and the second end. The tube may be inserted into a subject by inserting the first closed end through the nasal cavity and out of the mouth. The tube may be tightened to retract the soft palate and attached to the mouthgag or the attachment mechanism. The at least one slit may deform from a closed position to an open position when tension is applied to the tube. The opened slits are disposed in between the oral cavity and the nasal cavity. For example, the slits may be located around the soft palate.

The method of the present invention may further include attaching the tube near the first end to the tube near the second end using the attachment component. For example, the first end of the tube may fit through the opening through the tab, thereby securing the first end out of the way of the operation and tightening the tube to retract the soft palate. As mentioned above the second open end may include a fitting. The method of treatment may further include attaching a vacuum tube to the fitting. The vacuum may be turned one so that fumes, smoke and debris within the oral or nasal cavities may be pulled through the at least one aperture.

It should be understood, of course, that the foregoing relates to exemplary embodiments of the invention and that modifications may be made without departing from the spirit and scope of the invention as set forth in the following claims.

What is claimed is:

1. A suction catheter comprising:
a flexible tube having a first end, a second end, and a cluster of slits formed through the flexible tube in between the first end and the second end, wherein each slit is defined by two inner edges perpendicular to the longitudinal axis of the flexible tube, wherein
the first end comprises a closed end and the second end comprises a fitting formed to releasably secure to a vacuum hose, and
each slit is provided in a closed position when the flexible tube is not subject to external stress, the closed position of each slit comprising the two inner edges abutting one another, wherein, when a tension is applied to the tube, one or more of the slits of the cluster of slits deform from the closed position to an open position, the open position comprising the two inner edges separated from one another to form opened slits,
wherein the opened slits are configured to remove fumes and debris when the suction tube is under a vacuum.

2. The suction catheter of claim 1, further comprising an attachment mechanism attached to the tube at the second end and configured to releasable secure the tube to itself in a looped configuration.

3. The suction catheter of claim 2, wherein the attachment mechanism comprises a tab extending from the tube and comprising an opening through the tab formed to receive and secure the tube within.

4. The suction catheter of claim 1, wherein the cluster of slits is located near a center point in between the first end and the second end.

5. The suction catheter of claim 4, wherein the cluster of slits are oriented circumferentially around the tube and adjacent to one another.

6. A method of treatment comprising the steps of:
providing a flexible tube comprising a first closed end, a second open end and a cluster of slits formed through the tube in between the first closed end and the second open end, wherein each slit is defined by two inner edges perpendicular to the longitudinal axis of the flexible tube;
inserting the first closed end through a nasal cavity, through an oral cavity and out of a mouth of a user;
positioning the cluster of slits in between the oral cavity and the nasal cavity adjacent to a soft palate of the user;
wherein each slit is provided in a closed position when the flexible tube is not subjected to external stress, and
pulling the tube against the soft palate, thereby retracting the soft palate and deforming one or more of the plurality of slits from a closed position comprising the two inner edges of each slit abutting one another to an open position comprising the two inner edges separate from one another to form opened slits,
wherein the opened slits are configured to remove fumes and debris when the suction tube is under a vacuum.

7. The method of claim 6, further comprising the step of: attaching the first closed end of the tube to an attachment mechanism extending from the second open end of the tube.

8. The method of claim 7, wherein the attachment mechanism comprises a tab extending laterally from the second end, wherein the tab comprises an opening therethrough, wherein the tube is inserted through the opening.

9. The method of claim 6, further comprising the step of attaching a vacuum hose to the second open end.

10. The method of claim 6, wherein the cluster of slits are oriented circumferentially around the tube and adjacent to one another.

\* \* \* \* \*